United States Patent
Oser

(10) Patent No.: US 6,615,504 B2
(45) Date of Patent: Sep. 9, 2003

(54) APPARATUS AND METHOD FOR DETERMINING A CIRCUMFERENCE

(75) Inventor: Daniel Oser, Worthsee (DE)

(73) Assignee: DOMED Medizintechnik GmbH, Krailling (DE)

( * ) Notice: Subject to any disclaimer, the term of this patent is extended or adjusted under 35 U.S.C. 154(b) by 0 days.

(21) Appl. No.: 09/877,732

(22) Filed: Jun. 8, 2001

(65) Prior Publication Data

US 2002/0004992 A1 Jan. 17, 2002

(30) Foreign Application Priority Data

Dec. 10, 1998 (DE) .......................... 198 57 098

(51) Int. Cl.$^7$ ................................. G01B 3/10
(52) U.S. Cl. ........................ 33/555.4; 33/732; 33/512
(58) Field of Search ............... 33/511, 512, 514.1, 33/514.2, 555.1, 555.4, 815, 755, 759, 732, 734, 735, 743; 606/102, 201, 202, 203

(56) References Cited

U.S. PATENT DOCUMENTS

| | | | | |
|---|---|---|---|---|
| 1,404,601 A | * | 1/1922 | Gordon | 33/555.4 |
| 3,545,087 A | * | 12/1970 | Doyle, III et al. | 33/732 |
| 3,967,383 A | * | 7/1976 | Collins | 33/179 |
| 4,058,266 A | * | 11/1977 | Beery | 242/534.2 |
| 4,161,823 A | * | 7/1979 | Collins | 33/555 |
| 5,103,571 A | * | 4/1992 | Richards | 33/555.4 |
| 5,174,030 A | * | 12/1992 | Clot et al. | 33/3 C |

FOREIGN PATENT DOCUMENTS

GB  1594833  8/1981

OTHER PUBLICATIONS

Patent Abstract of German publication No. DE 32 23 711 A, published Jan. 5, 1984.
Patent Abstract of German publication No. DE 296 07 994 U, published Oct. 24, 1996.
International Search Report, application No. PCT/EP99/09080, mailed Apr. 4, 200.
International Search Report, Application No. PCT/EP99/09080, mailed Aug. 13, 2001 (English translation).

* cited by examiner

Primary Examiner—Diego Gutierrez
Assistant Examiner—Tania C. Courson
(74) Attorney, Agent, or Firm—Meyertons Hood Kivlin Kowert & Goetzel, P.C.; Jeffrey C. Hood

(57) ABSTRACT

The present invention relates to an apparatus and a method for determining the circumference of a body. In this case, the apparatus has at least the following elements: a wire which has a known length section of length $L_D$, a position sensor (4), which is in operative contact with the wire (5) such that it outputs a signal S, as soon as the wire (5) exerts at least a predetermined tensile force Z on the position sensor (4), a drive device (6, 7) for tensioning the length section of the length $L_D$ of the wire along the circumference (2) of the body (3), the drive device (6, 7) being connected to the position sensor (4) such that when the signal S is output, the wire (5) is no longer tensioned, and a distance meter (10), in operative contact with the drive device (6, 7), for measuring the distance $W_D$ traced by the wire (5) as it is tensioned along the circumference (2) of the body (3) by the drive device (6, 7), so that the circumference (2) of the body (3) can be determined from the length $L_D$, the distance $W_D$ and an apparatus-dependent geometry factor G. In addition, the invention relates to the use of the apparatus according to the invention and the method according to the invention for plethysmography, in particular for determining the circumference of extremities.

13 Claims, 1 Drawing Sheet

APPARATUS AND METHOD FOR DETERMINING A CIRCUMFERENCE

FIELD OF THE INVENTION

The present invention relates to an apparatus and a method for determining the circumference of a body.

DESCRIPTION OF THE RELATED ART

In virtually all technical areas, it is often necessary to determine or check the circumference of a body. In the area of production a circumference measurement is often part of a quality check on products. In this case, it is often important that this circumference determination is carried out as exactly as possible, but at the same time also quickly and simply, since it is most often only one measurement which accompanies the actual process and, in terms of time, is not intended to have a very detrimental effect on the fault-free progress of the process. A further application for a circumference meter is in the medical area. Here, for example in the area of venous occlusion plethysmography, it is necessary to be able to determine the exact circumference of any desired extremities of a patient.

DE 3 223 711 describes an apparatus and a method for measuring the lower extremities, for example as a basis for the preparation of medical compression hose, the circumferential measurement being carried out by using a measuring tape loop whose circumference can be varied by an electric-motor drive and which, when recording the circumferential dimension, encloses the extremities with a constant, electronically regulated contact pressure. With the aid of an electronic eye module sensing the measuring tape scale and a counter electrode, the measured result is displayed digitally. The drawback with this apparatus and this method is the complicated handling, since a closed measuring tape loop has to be slipped over or guided over the extremities to be measured. A further drawback consists in a measurement inaccuracy which increases with time as a result of the measuring tape moving to and fro during a measuring operation.

It is an object of the present invention to provide an apparatus and a method with which rapid, simple and accurate determination of the circumference of a body is possible.

According to the invention, this object is achieved by the apparatus described in the claims and by the method described in the method claims.

SUMMARY OF THE INVENTION

Within the context of the present invention, an apparatus for determining the circumference of a body is provided, the apparatus having at least the following elements:

a) a wire which has a known length section of length $L_D$,
b) a position sensor, which is in operative contact with the wire such that it outputs a signal S, as soon as the wire exerts at least a predetermined tensile force Z on the position sensor,
c) a drive device for tensioning the length section of the length $L_D$ of the wire along the circumference of the body, the drive device being connected to the position sensor such that when the signal S is output, the tensioning of the wire by the drive device can be stopped,
d) a distance meter, in operative contact with the drive device, for measuring the distance $W_D$ traced by the wire as it is tensioned along the circumference of the body by the drive device,
e) so that the circumference of the body can be determined by the length $L_D$, the distance $W_D$ and an apparatus-dependent geometry factor G.

It is preferable if the apparatus according to the invention has a unit for the calculation and output of the circumference of the body from the length $L_D$, the distance $W_D$ and an apparatus-dependent geometry factor G. This ensures rapid and simultaneously exact determination of the circumference. It is preferable if the distance meter is coupled directly to a signal processing unit, preferably to a microprocessor or, particularly preferably to a computer, in which the measured distance $W_D$ traced by the wire as it is tensioned along the circumference of the body by the drive device can be read in and evaluated directly. The parameters of the apparatus which are known in advance, such as the length $L_D$ of the known length section of the wire and the apparatus-dependent geometry factor G, can be stored in the signal processing unit as fixed variables and called up at any time, or, preferably, integrated directly into a program used for the evaluation. The resulting circumference then preferably appears on a monitor or display connected directly to the processing unit.

In another preferred embodiment of the apparatus according to the invention, the drive device is a mangle mechanism with a drive roller and a traction roller. The introduction of the wire between the drive roller and the traction roller means that the apparatus becomes intrinsically self-contained. The drive device, the wire and the position sensor therefore form an intrinsically self-contained, complete system for determining the circumference of a body around which the wire wraps. After the drive roller has been set operating, the wire functions as a transmitter of the torque from the drive roller to the traction roller, so that the two rollers rotate synchronously with each other and, in so doing, simultaneously draw in the wire. The length by which the wire is drawn in between the two rollers can simultaneously be measured at any time with the aid of the distance meter coupled to the traction roller. As soon as the wire has been tensioned, that is to say as soon as it rests directly on the body whose circumference is to be measured, the wire exerts a finite tensile force on the position sensor, with which it is in operative contact. The position sensor reacts to this tensile force acting on it by generating a signal. This signal is preferably in turn coupled back to the drive roller which, when the signal appears, stops operating, so that the wire is not drawn in further by the two rollers, that is to say the drive roller and the traction roller.

The position sensor used is preferably an inductive distance sensor, whose impedance changes as a function of the force acting on it, as a result of the wire in this case. Here, the force which is necessary for the position sensor to respond, lies far below the compressibility limit of the body, whose circumference is to be determined. This ensures that the body is not compressed by the wire, and therefore changes its circumference, before the position sensor responds, that is to say provides a signal. In order to ensure that the compressibility limit of the body still has not been reached during the circumference measurement, after the first signal provided by the position sensor, the wire is preferably drawn in further by the drive device by a specific amount. The comparison of the length of the wire that is drawn in and can be read off on the distance meter after the first signal provided by the position sensor, together with the corresponding length extension of the position sensor which occurs simultaneously after the first signal as the wire is drawn in further by the drive device, offers a good possible means of checking; this is because the two distances must be identical if the body has not been compressed by the wire now resting directly on the circumference of the body.

In a preferred embodiment, the drive device has an electric motor.

In a preferred embodiment of the apparatus according to the invention, at least part of the surfaces of the drive device which come into contact with the wire as it is tensioned along the circumference of the body has a roughening which can be achieved by photomechanical or mechanical or chemical or electrochemical treatment. In the previously mentioned preferred refinement of the drive device as a mangle mechanism, such deliberate roughening of the traction roller achieves good adhesion of the wire on the traction roller and therefore ensures that the wire is drawn in simple, continuously and steadily. In the case of the mangle mechanism, good adhesion between wire and traction roller is also indispensable for its satisfactory functioning, that is to say for the interplay of traction roller, drive roller and wire.

While the adhesion between wire and traction roller should be comparatively high, the adhesive and sliding friction of the wire on the circumference of the body to be determined must be comparatively small, so that the wire can slide along on the circumference satisfactorily as it is tensioned. It is therefore preferable for a smooth wire, in particular a nylon wire, to be chosen. Furthermore, a material, in particular nylon, is preferably selected for the wire, so that the cross-sectional area of the wire remains substantially constant, even under loading in wide limits. This results in a constant contact area between the wire and the traction roller and therefore constant process conditions. The wire preferably consists of a flexible material, in order to ensure a good material fit as the wire is tensioned around the circumference to be determined. Nylon is also well-suited as a wire material with regard to this material property. A further preferred material property for the wire is a high tearing strength. This property is also satisfied by nylon. To this extent, the wire which is used to wrap at least partly around the body along its circumference consists of nylon in a preferred embodiment of the invention. Nylon is a cost-effective but, at the same time, also a very stable, in particular tear-resistant smooth and flexible material. The wire is therefore very stable with respect to tensile forces acting on it over a wide range. When the wire is laid around the body and tensioned as a result of being pulled in by means of the interplay of drive roller and traction roller, there is therefore no risk, or only an extremely small risk, that the wire will tear before the determination of the circumference could be carried out. In addition, a wire material is preferably selected whose length change as a function of the temperature is vanishingly small. This property is also satisfied by nylon.

In a further preferred embodiment of the invention, use is made of a highly sensitive sensor which reacts at a very low tensile force exerted on it by the wire, that is to say provides a signal. It is preferable if, as already mentioned, an inductive distance sensor is used here. It is therefore possible, with the aid of the present invention, even to determine the circumference of such bodies which have a finite compressibility, that is to say are not rigid. Such bodies have to be handled, for example, in the case of extremities. In the area of occlusion and/or compression phlethysmography, it is necessary to determine the circumference of extremities as a function of the state of the corresponding vessels. Depending on the state and function of the vessels, the circumference of the extremities can vary. With the aid of the present invention, these often very small but significant changes in circumference can be determined very accurately, that is to say with a resolution of about 1 $\mu$m, and quickly.

In addition, the present invention relates to a corresponding method of determining the circumference of a body, the method having at least the following steps.

a) Laying a wire with a known length section of length $L_D$ around the body in the circumferential direction, the wire being in operative contact with a position sensor such that the position sensor outputs a signal S as soon as the wire exerts at least a predetermined tensile force Z on the position sensor, b) Introducing the wire into a drive device which is in operative contact with a distance meter, c) Tensioning the wire along the circumference of the body by starting the drive device, until the position sensor in operative contact with the wire provides a signal, d) Reading the distance $W_D$, determined with the distance meter, traced by the wire as it is tensioned along the circumference of the body by the drive device, e) Determining the circumference of the body from the length $L_D$, the distance $W_D$ and an apparatus-dependent geometry factor G.

In addition, the present invention relates to the use of the apparatus according to the invention and of the method according to the invention in the area of occlusion and/or compression phlethysmography, in particular for determining the circumference of extremities.

BRIEF DESCRIPTION OF THE DRAWINGS

The apparatus according to the invention and the method according to the invention will now be described using the following FIGURE, in which.

DETAILED DESCRIPTION OF THE EMBODIMENTS

Figure 1:
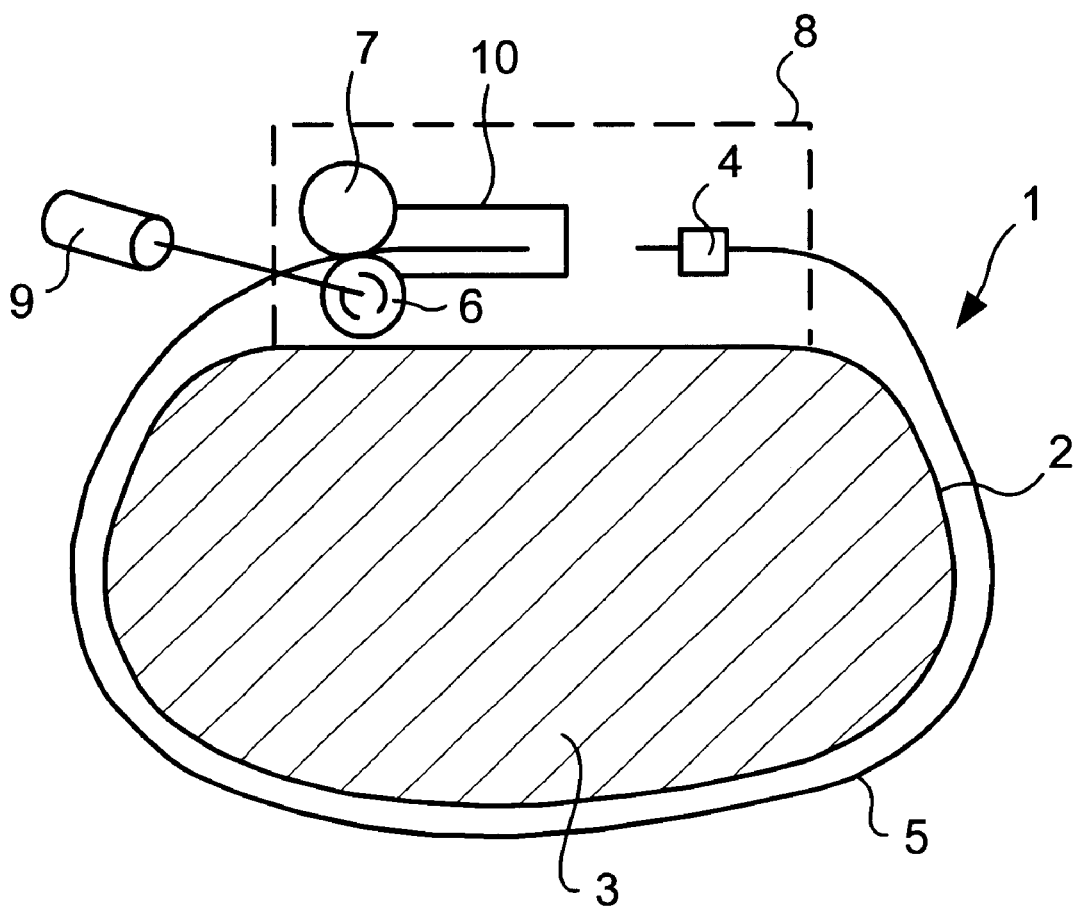
FIG. 1 shows a simplified representation of an apparatus according to the invention, for determining the circumference of a body.

FIG. 1 shows a simplified representation of an apparatus 1 according to an embodiment of the invention for determining the circumference 2 of a body 3. First of all, the apparatus 1 is arranged at a point on the circumference 2 of the body 3 to be measured. Arranged on the position sensor 4 of the apparatus 1 according to the invention is a wire 5 having a known length section of length $L_D$ which, to determine the circumference 2 of the body 3, is laid around the body 3 in its circumferential direction, that is to say the wire 5 at least partly wraps around the body 3 along the circumference 2 to be measured. The wire 5 is then introduced between a drive roller 6 and a traction roller 7 which together form the drive unit of the apparatus 1. The traction roller 7 is coupled to a distance meter (10). The drive roller 6 is driven by a drive 9, preferably an electric motor. The position sensor 4, the drive roller 6 and the traction roller 7 together with the distance meter (10) are surrounded by a housing 8. As soon as the wire has been introduced between the two rollers, the apparatus is closed. By means of the drive, the drive roller 6 is set rotating. Via the wire 5, which functions here as a transmitter, the torque of the drive roller 6 is transmitted to the traction roller 7, so that the two rollers rotate synchronously with each other and, in so doing, also draw in the wire 5. As a result, the wire 5, which at its other end is connected to the position sensor 4, is gradually tensioned until it rests with a material fit on the circumference 2 of the body 3. As soon as the wire 5 is resting directly on the body 3, the wire 5 exerts a tensile force on the position sensor 4, which in turn has the effect that the latter generates a signal as soon as the tensile force exerted by the wire corresponds to a predetermined tensile force. Associated with the signal, the operation of the drive roller 6 is interrupted, that is to say the wire 5 is not tensioned further. With the aid of the distance meter (10), it is now possible for the length $L_D$ of the distance which the wire 5 has traced as it is tensioned along the circumference 2 of the body 3 by the two rollers 6, 7 to be read off exactly. With the knowledge of the total length $L_D$ of that length section of the wire 5, which is accessible to the distance measurement with the aid of a distance meter (10), and of the apparatus-dependent geometry factor G, it is then possible to calculate back very quickly and simply to the circumference 2 of the body 3:

$$L_D - W_D + G = \text{circumference 2}.$$

Therefore, to summarize, the present invention relates to an apparatus and a method for determining the circumference of a body. In this case, the apparatus has at least the following elements: a wire which has a known length section of length $L_D$, a position sensor (4), which is in operative contact with the wire (5) such that it outputs a signal S, as soon as the wire (5) exerts at least a predetermined tensile force Z on the position sensor (4), a drive device (6, 7) for tensioning the length section of the length $L_D$ of the wire along the circumference (2) of the body (3), the drive device (6, 7) being connected to the position sensor (4) such that when the signal S is output, the wire (5) is no longer tensioned, and a distance meter (10), in operative contact with the drive device (6, 7), for measuring the distance $W_D$ traced by the wire (5) as it is tensioned along the circumference (2) of the body (3) by the drive device (6, 7), so that the circumference (2) of the body (3) can be determined from the length $L_D$, the distance $W_D$ and an apparatus-dependent geometry factor G.

The method has at least the following steps: laying a wire (5) with a known length section of length $L_D$ around the body (3) in the circumferential direction, the wire (5) being in operative contact with a position sensor (4) such that the position sensor (4) outputs a signal S as soon as the wire (5) exerts at least a predetermined tensile force Z on the position sensor (4), introducing the wire (5) into a drive device (6, 7) which is in operative contact with a distance meter (10), tensioning the wire (5) along the circumference (2) of the body (3) by starting the drive device (6, 7), until the position sensor (4) in operative contact with the wire (5) provides a signal, reading the distance $W_D$, determined by the distance meter (10), traced by the wire (5) as it is tensioned along the circumference (2) of the body (3) by the drive device (6, 7), determining the circumference (2) of the body (3) from the length $L_D$, the distance $W_D$ and an apparatus-dependent geometry factor G.

In addition, the invention relates to the use of the apparatus according to the invention and the method according to the invention for plethysmography, in particular for determining the circumference of extremities.

Although the system and method of the present invention has been described in connection with the preferred embodiment, it is not intended to be limited to the specific form set forth herein, but on the contrary, it is intended to cover such alternatives, modifications, and equivalents, as can be reasonably included within the spirit and scope of the invention as defined by the appended claims.

What is claimed is:

1. A device (1) for determining the circumference (2) of a body (3), the apparatus (1) having at least the following elements:
    a) a wire (5) which has a loose end and which has a known length section of length $L_D$,
    b) a position sensor (4), which is in operative contact with the wire (5) such that it outputs a signal S, as soon as the wire (5) exerts at least a predetermined tensile force Z on the position sensor (4),
    c) a drive device (6, 7) for drawing in the loose end of the wire (5) and for tensioning the length section of the length $L_D$ of the wire (5) along the circumference (2) of the body (3), the drive device (6, 7) being connected to the position sensor (4) such that when the signal S is output, the tensioning of the wire (5) by the drive device (6, 7) is stopped,
    d) a distance meter (10), in operative contact with the drive device (6, 7), for measuring the distance $W_D$ traced by the wire (5) as it is tensioned along the circumference (2) of the body (3) by the drive device (6, 7),
    e) so that the circumference (2) of the body (3) is determined from the length $L_D$, the distance $W_D$ and an apparatus-dependent geometry factor G.

2. The apparatus as claimed in claim 1, characterized in that the apparatus has a unit for the calculation and output of the circumference (2) of the body (3) from the length $L_D$, the distance $W_D$ and the apparatus-dependent geometry factor G.

3. The apparatus as claimed in one of the preceding claims, characterized in that the drive device (6, 7) is a mangle mechanism with a drive roller (6) and a traction roller (7).

4. The apparatus of claim 1, wherein one or more surfaces of the drive device (6, 7) that come into contact with the wire (5) are roughened.

5. The apparatus of claim 1, wherein the wire (5) comprises a nylon wire.

6. The apparatus of claim 1, wherein the drive device (6, 7) comprises an electric motor (9).

7. A method of determining the circumference (2) of a body (3), which has at least the following steps:
    a) Laying a wire (5) with a known length section of length $L_D$ around the body (3) in the circumferential direction, the wire (5) being in operative contact with a position sensor (4) such that the position sensor (4) outputs a signal S as soon as the wire (5) exerts at least a predetermined tensile force Z on the position sensor (4),
    b) Introducing the wire (5) into a drive device (6, 7) which is in operative contact with a distance meter (10),
    c) Tensioning the wire (5) along the circumference (2) of the body (3) by starting the drive device (6, 7), until the position sensor (4) in operative contact with the wire (5) provides a signal,
    d) Reading the distance $W_D$, determined by the distance meter (10), traced by the wire (5) as it is tensioned along the circumference (2) of the body (3) by the drive device (6, 7),
    e) Determining the circumference (2) of the body (3) from the length $L_D$, the distance $W_D$ and an apparatus-dependent geometry factor G.

8. A device (1) for determining the circumference (2) of a body (3), comprising:

a wire (5) comprising a loose end and at least one section having a known length;

a position sensor (4) coupled to the wire (5), wherein the position sensor (4) is configured to generate an output signal when the wire (5) exerts at least a predetermined tensile force on the position sensor (4);

a drive device (6,7) configured to pull in the loose end of the wire (5) and further configured to tension at least a section of the wire (5), wherein the drive device (6,7) is coupled to the position sensor (4) such that when an output signal is generated by the position sensor (4) the drive device (6,7) is inhibited from further tensioning the wire (5); and a distance meter (10) coupled to the drive device (6,7), wherein the distance meter (10) is configured to determine the distance traced by the wire (5) as the wire (5) is tensioned by the drive device (6,7) to determine the circumference (2) of the body (3).

9. The device of claim 8, further comprising an output unit, wherein the output unit is configured to provide output corresponding to the circumference (2) of a body (3) based on the length of at least one section of the wire (5) having a known length, the distance traced by the wire (5) as the wire (5) is tensioned by the drive device (6,7) and an apparatus-dependent geometry factor.

10. The device of claim 8, wherein the drive device (6,7) comprises at least one roller, and wherein at least a portion of at least one roller configured to contact the wire (5) is not smooth.

11. The device of claim 8, wherein the wire (5) comprises a nylon wire.

12. The device of claim 8, the drive device (6,7) comprises an electric motor (9).

13. A method of determining the circumference (2) of a body (3), comprising:

positioning a wire (5) around a body (3), wherein the wire (5) comprises at least a section of known length;

pulling the wire (5) using a drive device (6,7), until a predetermined tension is achieved;

determining the distance traced by the wire (5) as the wire (5) is pulled by the drive device (6,7); and determining the circumference (2) of the body (3) based at least in part on the known length of at least one section of the wire (5), the distance traced by the wire (5) as the wire (5) is pulled by the drive device (6,7) and an apparatus-dependent geometry factor.

* * * * *

UNITED STATES PATENT AND TRADEMARK OFFICE
CERTIFICATE OF CORRECTION

PATENT NO. : 6,615,504 B2  Page 1 of 1
DATED : September 9, 2003
INVENTOR(S) : Daniel Oser It is certified that error appears in the above-identified patent and that said Letters Patent is hereby corrected as shown below:

<u>Column 6,</u>
Line 8, please delete "a signal 5" and substitute -- a signal S --.

Signed and Sealed this

Twenty-third Day of December, 2003

JAMES E. ROGAN
*Director of the United States Patent and Trademark Office*